April 29, 1975 O. L. WEEKS Plant Pat. 3,710
ROSE PLANT
Filed March 21, 1974
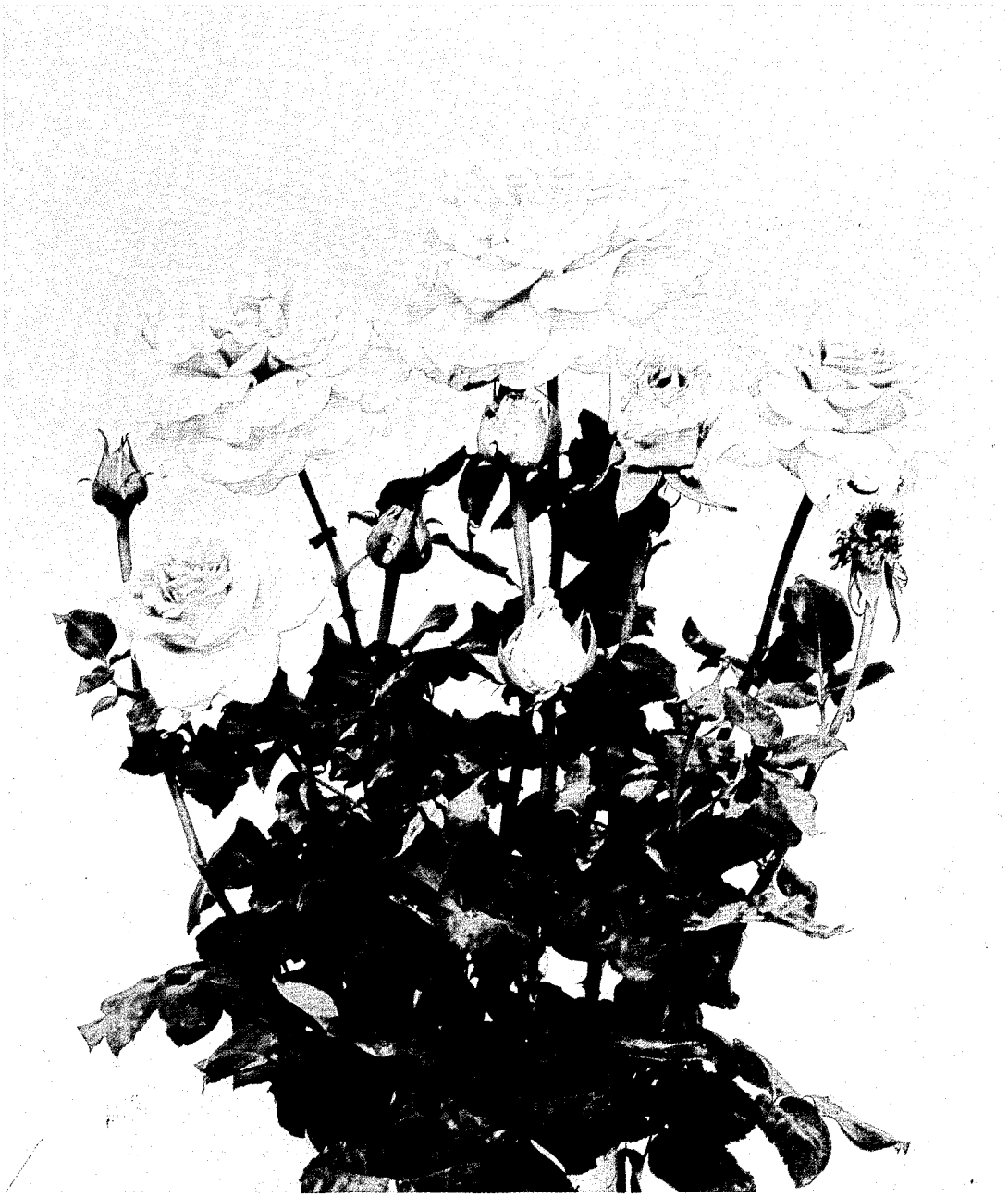

United States Patent

Plant Pat. 3,710

Patented Apr. 29, 1975

3,710

ROSE PLANT

O. L. Weeks, 926 W. Philadelphia, Ontario, Calif. 91762

Filed Mar. 21, 1974, Ser. No. 453,386

Int. Cl. A01h *5/00*

U.S. Cl. Plt.—11 1 Claim

The present invention relates to a new and distinct variety of rose plant of the hybrid grandiflora class, which was originated by me by crossing two unnamed and unpatented rose seedlings, respectively identified in my breeding records as #6276–2 and #6486–1, the former being the seed parent and the latter the pollen parent.

As the result of this breeding, I have produced a new and improved rose variety which is distinguished from its parents, as well as from all other rose varieties of which I am aware, as evidenced by the following unique combination of characteristics which are outstanding in the new variety:

(1) A sturdy, vigorous and upright habit of growth;
(2) Exceptionally heavy and glossy foliage which is considerably above average in mildew resistance;
(3) Straight and strong canes which support the blooms with no tendency to weak necks;
(4) An interesting and attractive flower form which is of extreme interest to flower arrangers; and
(5) An unusual blending of yellow flower colors of muted butterscotch and brownish yellows which, in the open flowers, form darker petals at the flower center with lighter outer petals ringing the center petals as a consistent trait independent of the aging process or weather conditions.

In comparison with its pollen parent, the plant of my new variety is far more vigorous and its foliage is of much better quality; its flowers are larger and of better form; and the blending of muted butterscotch and brownish yellows of the flower colors is very unusual and distinctive in comparison with the clear yellow flower color of this parent.

As compared with its seed parent, the plant of my new variety is far more vigorous and bears larger foliage which is of better substance; it is more prolific in blooming habit; and the flower colors of the new variety form a distinctive blend of muted butterscotch and brownish yellows in contrast with the pure and even paler yellow flower color of this parent.

Asexual reproduction of my new rose variety by budding, as performed by me at Ontario, Calif., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably posible to make the same in a color illustration of this character.

The following is a detailed description of my new variety, with color terminology in accordance with Munsell's Color Cascade, published by Munsell Color Company, Inc., of Baltimore, Md., except where general color terms of ordinary dictionary significances are obvious:

Type: Hardy; tall; bush; for cut flowers and for garden decoration.
Class: Hybrid grandiflora.
Breeding: Seedling.
*Seed parent.*—An unnamed seedling.
*Pollen parent.*—An unnamed seedling.
Propagation: Holds its distinguishing characteristics through succeeding propagations by budding.

FLOWERS

Locality where grown and observed: Ontario, Calif.
Flowers borne: Singly and 2 or 3 to stem in pyramidal clusters; on strong stems of medium to long length.
Quantity of bloom: Free and abundant, both outdoors and in greenhouse.
Continuity: One season; from intermittent to continuous.
Frangrance: From slight to moderate.
Bud:
*Peduncle.*—Short; heavy caliper; erect; stiff; entirely smooth. Color—from light to medium green.
*Before calyx breaks.*—Size—medium.
Form—medium length; pointed; with a conspicuous neck; with foliaceous appendages on the surface of the bud; with bristle-like foliaceous parts extending beyond the tip of the bud equal to ¼ to ½ or more of its length.
*As the calyx breaks.*—Color—Light Yellow, between 29–5 and 29–6 but stronger yellow, with a tinge of Strong Pink, 38–5, lightening near tip.
*As petals first open.*—Size—small. Form— short; entirely round. Color—Outside—between Strong Yellow, 27–5 and 27–6 with Greenish Yellow, between 23–6 and 23–7 ribbing and tipped with Strong Pink, between 38–5 and 38–6. Inside—from Strong Yellow, 27–5 to 27–6 to 27–7 with Pink Tinge at apex between 38–5 and 38–6.
*Opening.*—Opens up well.
Bloom:
*Size (when fully open).*—From 3 inches to 4½ inches.
*Petalage.*—Many petals, usually with no stamens showing; from 38 to 44 petals; arranged regularly.
*Form.*—Flat, with full center essentially globular at first, but becoming flat globular and high-centered; petals being at first tightly cupped and rolled inward, but later becoming loosely cupped and rolled outward at maturity.
Petals:
*Texture.*—Fairly thin and soft.
*Appearance.*—Inside—velvety. Outside—velvety.
*Shape.*—Outside—round, with apex flat. Intermediate—round, with apex flat. Inside—round, with apex flat.

This description of a newly opened flower was made from a rose grown outdoors during the month of October at Ontario, Calif.:

*Color.*—Outer petal—Outside surface—Strong Yellow, between 27–5 and 27–6 at base, blending into deeper Yellow, 29–5, with further blending half-way to apex to Pale Yellow, 27–1, with a faint shading on tip of Medium Pink, 38–6, but brighter. Inside surface—Strong Yellow, 27–6 but brighter, at base, blending to Orange Yellow, between 31–5 and 31–6, with Pink ribbing 38–6 and with a further blending half-way to apex of very Pale Yellow, 29–1 and continuing with a Pink shading of 38–6. Intermediate petal—Outside surface—between Strong Yellow, between 27–6 and 27–7 and deeper Yellow, 29–6 at base, blending at apex to completely Pale Yellow, 27–1, with a faint pink tip of brighter than Medium Pink, 38–6. Inside surface—between Strong Yellow, 27–5 and 27–6 at base, blending into Medium Pink, 31–6 and with a further blending at apex of deep Orange Yellow, 32–5 with a faint tip of Medium Pink 38–6, but brighter. Inner petal—Outside surface—Strong Yellow, between 29–6 and 29–7, but a little darker, at base, with a small segment at tip of apex of Medium Pink, 38–6 but brighter. Inside surface—small arc at base of Strong Yellow, 27–6, blending into Medium Pink, between 31–7 and 31–8 but darker, with a small segment at tip of apex of Medium Pink, 38–6, but brighter.

This description was made from a rose that was open for three days outdoors during the month of October at Ontario, Calif.:

*Color.*—Outer petal—Outside surface—basal segment of Medium to Strong Yellow, between 27–3 and 27–4, blending into Pale Yellow, between 27–1 and 28–1 but brighter and further blending to between 26–5 and 26–6. Inside surface—basal segment between slightly greenish yellow and medium yellow, blending into extremely Pale Yellow, between 27–1 and 28–1. Inner petal—Outside surface—Strong Yellow, between 27–5 and 27–6 at base, blending upward into Orange Yellow, between 31–4 and 31–5 but somewhat lighter. Inside surface—Strong to Deep Yellow, 28–5 and 27–6 at base, blending upward into Orange Yellow, between 31–4, 31–5 and 35–5, with a slight pink tinge.

*General color effect.*—Newly opened flower—essentially Yellowish Orange, between 29–6, 29–7 and 31–6, with a tinge of Strong Pink at apex between 38–5 and 38–6. 3-days open—blend of extremely Pale Yellow, 27–1, 31–4 and 32–4, with a tinge of Strong Pink near apex between 38–5 and 38.6.

*Behavior.*—Drop off cleanly.

*Flower longevity.*—On bush in garden—3 or 4 days in October. Cut roses grown outdoors and kept at living room temperature—from 2 to 4 days in October.

REPRODUCTIVE ORGANS

Stamens: Many; arranged irregularly about pistils; tucked in calyx.

Filaments: Long; most with anthers. Color—Yellow.

Anthers: Large; all open essentially at once. Color—Yellow.

Pollen: Abundant. Color—Golden yellow.

Pistils: From medium in number to many.

Styles: Very uneven; very short; thin caliper; bunched.

Stigma: Color—Yellowish.

Ovaries: All enclosed in calyx.

Hips: None observed.

Sepals: Permanent; moderately long; spear-shaped; recurved. Color—Medium green.

Seeds: None observed.

PLANT

Foliage:

*Leaves.*—Compound of 3–5 leaflets; abundant; medium size; with some moderately leathery and somewhat glossy; wrinkled.

*Leaflets.*—Shape—Ovate. Apex—from obtuse to acute. Base—Round. Margin—finely serrate.

*Color.*—Mature—Upper surface—moderately dark green. Under surface—moderately light green. Young—Upper surface—normal green, with bronze-red overtones. Under surface—light green, with bronze-red overtones.

*Rachis (the supporting stem of the compound leaf).*—Medium weight. Upper side—smooth. Under side—mildly prickly.

*Stipules.*—Medium length; moderately wide; points of medium length turning out at an angle of from 45° to 90°.

Disease and insect resistance: Average resistance to usual rose insects, but better than average resistance to powdery mildew, as determined from comparison with other rose varieties grown under the same conditions at Ontario, Calif.

Growth:

*Habit.*—Tall; bushy; upright; much branched.

*Growth.*—Free and vigorous.

*Canes.*—From medium to heavy caliper.

*Main stems.*—Color—dull and fairly light green. Large prickles—several; from short to medium length; straight; with short, narrow round base. Color—brown. Small prickles—several. Color—brown. Hairs—None.

*Branches.*—Color—light green. Large prickles—several; medium long; essentially straight, with a minimum of some slight downward hooking. Color—light brown at base, blending into yellowish green. Small prickles—None. Hairs—None.

*New shoots.*—Color—dull green. Large prickles—several; medium long; essentially straight, with a minimum of some slight downward hooking; with narrow elongated base of medium length. Color—light brown at base, blending into yellowish green. Small prickles—None. Hairs—Some. Color—from grey to green.

I claim:

1. A new and distinct variety of rose plant of the hybrid grandiflora class, substantially as herein shown and described, characterized particularly as to novelty by the unique combination of a sturdy, vigorous and upright habit of growth, exceptionally heavy and glossy foliage which is considerably above average in mildew resistance, straight and strong canes which support the blooms with no tendency to weak necks, an interesting and attractive flower form which is of extreme interest to flower arrangers, and an unusual blending of yellow flower colors of muted butterscotch and brownish yellows which, in the open flowers, form darker petals at the flower center with lighter outer petals ringing the center petals as a consistent trait independent of the aging process or weather conditions.

No references cited.

ROBERT E. BAGWILL, Primary Examiner